(12) United States Patent
De Villiers et al.

(10) Patent No.: US 10,421,986 B2
(45) Date of Patent: Sep. 24, 2019

(54) METHOD FOR THE CLARIFICATION OF HIGH-DENSITY CRUDE CELL CULTURE HARVEST

(71) Applicant: Janssen Vaccines & Prevention B.V., Leiden (NL)

(72) Inventors: Ann-Marie De Villiers, Leiden (NL); Charles Maria Hubert Hensgens, Alphen aan den Rijn (NL)

(73) Assignee: Janssen Vaccines & Prevention B.V., Leiden (NL)

( * ) Notice: Subject to any disclaimer, the term of this patent is extended or adjusted under 35 U.S.C. 154(b) by 313 days.

(21) Appl. No.: 15/024,954

(22) PCT Filed: Sep. 29, 2014

(86) PCT No.: PCT/EP2014/070786
§ 371 (c)(1),
(2) Date: Mar. 25, 2016

(87) PCT Pub. No.: WO2015/044418
PCT Pub. Date: Apr. 2, 2015

(65) Prior Publication Data
US 2016/0222429 A1   Aug. 4, 2016

(30) Foreign Application Priority Data
Sep. 30, 2013   (EP) ..................... 13186692

(51) Int. Cl.
| C12P 21/00 | (2006.01) |
| C12N 1/02 | (2006.01) |
| C07K 16/00 | (2006.01) |
| C07K 16/06 | (2006.01) |

(52) U.S. Cl.
CPC .......... *C12P 21/005* (2013.01); *C07K 16/065* (2013.01); *C12N 1/02* (2013.01)

(58) Field of Classification Search
CPC ........ C12P 21/005; C12N 1/02; C07K 16/065
See application file for complete search history.

(56) References Cited

U.S. PATENT DOCUMENTS

| 5,994,128 A | 11/1999 | Fallaux et al. |
| 7,291,484 B2 | 11/2007 | Yallop |
| 2010/0075413 A1 | 3/2010 | Zijlstra et al. |
| 2012/0064623 A1 | 3/2012 | Zijlstra et al. |
| 2012/0149063 A1 | 6/2012 | Zijlstra et al. |
| 2012/0149107 A1 | 6/2012 | Zijlstra et al. |
| 2013/0095527 A1 | 4/2013 | Zijlstra et al. |
| 2013/0244283 A1 | 9/2013 | Robin |
| 2014/0154745 A1 | 6/2014 | Zijlstra et al. |

FOREIGN PATENT DOCUMENTS

| WO | 2004099396 A1 | 11/2004 |
| WO | 2005095578 A1 | 10/2005 |
| WO | 2008006494 A1 | 1/2008 |
| WO | 2010043700 A1 | 4/2010 |
| WO | 2011045381 A1 | 4/2011 |
| WO | 2012045769 A1 | 4/2012 |
| WO | 2015044418 A1 | 4/2015 |

OTHER PUBLICATIONS

Clicke et al. Study of a recombinant CHO cell line producing a monoclonal antibody by ATF or TFF external filter perfusion in a WAVE BioreactorTM. 22nd European Society for Animal Cell Technology (ESACT) Meeting on Cell Based Technologies Vienna, Austria. May 15-18, 2011 (Year: 2011).*
Amersham brochure. Chapter 1. Selecting a hollow fiber cross flow membrane cartridge. Selecting Hollow Fiber Cartridges and Systems. Amersham Biosciences. downloaded from web.archive.org/web/20070824074237/http://wolfson.huji.ac.il/purification/PDF/dialysis/PHARMACIA_Ultrafiltration.pdf. p. 1-3 (Year: 2007).*
Perfusion-Cell Technology Group. 2015. p. 1-2 (Year: 2015).*
Hober et al. Protein A chromatography for antibody purification. Journal of Chromatography B, 848 (2007) 40-47 (Year: 2007).*
Pollock et al, Fed-Batch and Perfusion Culture Processes: Economic, Environmental, and Operational Feasibility Under Uncertainty, Biotechnology and Bioengineering vol. No. 1, Jan. 2013, Wiley.
Chinese Office Action, application No. 201480053396.4, dated Apr. 5, 2017, 6 pages.
Kuczewski et al., A single-use purification process for the production of a monoclonal antibody produced in a PER.C6 human cell line, Biotechnology Journal, Jan. 2011, pp. 56-65, vol. 6, No. 1.
PCT International Search Report, PCT/EP2014/070786, dated Nov. 6, 2014.
PCT International Written Opinion, PCT/EP2014/070786, dated Nov. 6, 2014.
Van Reis R et al., Industrial Scale Harvest of Proteins from Mammalian Cell Culture by Tangential Flow Filtration, Biotechnology and bioengineering, vol. 38, p. 413-422 (1991).
Kamen et al., Development and optimization of an adenovirus production process, J Gene Med 2004; 6: S18-S192.
Shukla et al., Downstream processing of monoclonal antibodies, Application of platform approaches, Journal of Chromatography B, 848 (2007) 28-39.
Morenweiser, Downstream processing of viral vectors and vaccines, Gene Therapy (2005) 12, S103-S110.
Schirmer et al., Primary Clarification of Very High-Density Cell Culture Harvests by Enhanced Cell Settling, Bioprocess International, Jan. 2010, p. 32-39.
"Amersham Brochure", Hollow Fiber Cartridges and Systems, Amersham Biosciences Inc. (2003).
Jayapal, et al., "Recombinant Protein Therapeutics from CHO Cells—20 Years and Counting", CHO Consortium—SBE Special Section, pp. 40-47, (2007).
Liu, et al. "Recovery and purification process development for monoclonal antibody production", mAbs, 2:5, 480-499, DOI:10.4161/mabs2.5.12645 (2010).

(Continued)

*Primary Examiner* — Taeyoon Kim
(74) *Attorney, Agent, or Firm* — Kramer Amado P.C.

(57) ABSTRACT

The disclosure provides methods for the clarification of a cell broth with high cell density.

17 Claims, 1 Drawing Sheet

(56) References Cited

OTHER PUBLICATIONS

Schirmer, et al., "Primary Clarification of Very High-Density Cell Culture Harvests by Enhanced Cell Settling", BioProcess International, pp. 32-39. (Jan. 2010).

Wurm, "Production of recombinant protein therapeutics in cultivated mammalian cells", Nature Biotechnology, vol. 22, No. 11, pp. 1393-1398. (Nov. 2004).

\* cited by examiner

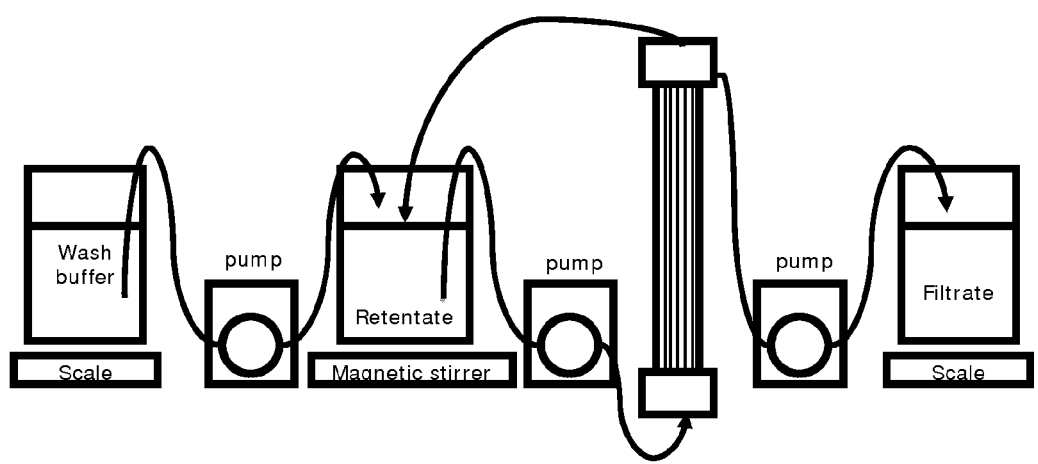

METHOD FOR THE CLARIFICATION OF HIGH-DENSITY CRUDE CELL CULTURE HARVEST

CROSS-REFERENCE TO RELATED APPLICATIONS

This application is a national phase entry under 35 U.S.C. § 371 of International Patent Application PCT/EP2014/070786, filed Sep. 29, 2014, designating the United States of America and published in English as International Patent Publication WO 2015/044418 A1 on Apr. 2, 2015, which claims the benefit under Article 8 of the Patent Cooperation Treaty to European Patent Application Serial No. 13186692.3, filed Sep. 30, 2013.

TECHNICAL FIELD

The application relates to the field of cell culture purification. More particularly, it concerns improved methods for the clarification of a crude cell culture harvest with high cell density.

BACKGROUND

Recent developments in the field of the production of biological substances, such as biopharmaceuticals, vaccines and antibodies, have created the need for large-scale manufacturing. Robust and high-yield processes are needed to support the world with sufficient amounts of biological substances to combat all kinds of diseases.

For that reason, great efforts are being put into the optimization of cell-based processes for the production of biological substances. In these processes, cells are being cultured at increasing densities in order to obtain higher product yields per volume. Such high cell density processes are being disclosed in, e.g., WO 2004/099396, WO 2005/095578 or WO 2008/006494. The contents thereof are incorporated herein by reference.

WO 2008/006494 discloses processes for the culturing of cells that produce a biological substance in a bioreactor wherein the cell culture is circulated over a separation system. The separation system separates the cells and the biological substance from substances having a lower molecular weight than the biological substance. The cells and the biological substance are retained together in the reactor and are not separated from each other.

WO 2005/095578 discloses processes for the culturing of cells that produce a biological substance in a bioreactor wherein the cell culture is circulated over a filter module, resulting in an outflow of liquid having a lower cell density than the cell culture and comprising the biological substance. The concentration of cells and biological substance in the outflow are substantially lower than in the bioreactor because the perfusion rate ranges between 1 and 13.7 L/day over a period of 23 days (i.e., the processed volume is 20 times higher than the volume of the bioreactor).

The optimized cell culture processes rely on the ability to culture cells at high cell density (e.g., higher than $10 \times 10^6$ cells/ml) with preservation of a high productivity per cell. Herewith, they offer a method to obtain a harvested solution with high concentration of proteins (e.g., antibodies) in a single bioreactor.

Processes wherein cells are cultured at high densities are prone to the accumulation of high amounts of cell debris and other impurities. These contaminants, together with the cells, have to be discarded further down the purification process, which is a cumbersome operation. As a first step, solid material (such as the cells) and cell debris are to be separated from the cell broth fluid, a step called "clarification." Examples of clarification methods used to date include centrifugation, filtration (such as microfiltration, depth filtration and filtration through absolute pore size membranes) and expanded bed chromatography.

Many methods for purifying biological substances such as antibodies have been described earlier, e.g., in van Reis et al. (*Biotechnology and Bioengineering*, 1991, Vol. 38, pp. 413-422). This reference describes a process comprising the steps of recovering cell culture fluid from fermenters and performing a cell-protein separation by tangential flow filtration. This method was, however, only performed with low-density cell cultures comprising about $0.5-4 \times 10^6$ cells/mL. It was not disclosed, nor expected hitherto, that such processes could be applied for a culture containing high cell densities. To the contrary, a strong suggestion could be inferred from the prior art that this process could not be applied on cultures containing high cell densities. In WO 2011/045381, for instance, which relates to the field of virus production, attempts have been made to directly clarify cell cultures having high cell density (see Example 1 of WO 2011/045381). During this attempt, a proper clarification could not be achieved due to rapid clogging of the filter. Apparently, the high cell densities of the broth that was processed impeded the purification step and rendered the tangential flow filtration (TFF) unsuitable for direct clarification. It was only after treatment of the high cell density broth with TRITON® (for lysing the cells), followed by domiphen bromide (DB), that the cell broth could be further processed (by clarification). The crude cell culture was not processed by TFF directly after harvest.

Based on these results, the skilled person would have been discouraged to treat a high cell density harvest directly (without pre-treatment) onto a clarification filter, expecting it to block rapidly.

Methods that are currently in use and considered state of the art for the treatment of high cell density cultures are, for instance, described in WO 2010/043700 or in Schirmer et al. (*Bioprocess International*, January 2010, pp. 32-39). The latter reference relates to a process wherein the harvest is first diluted, subsequently mixed with Si-PEI beads, after which the beads settle and the supernatant is removed and filtered by depth filtration.

Drawbacks of this method are that the harvest is first diluted 3-5 times depending on the cell concentration in the harvest, which implies that also the antibody titers are diluted 3-5 times. Second, the chromatography resins used in large amounts during the process are very expensive and cannot be re-used. Finally, from experience with this technique, it has been seen that the recovery is variable.

Since cell culture processes are being up-scaled and cells are being cultured at increasing densities, there is a need in the industry for downstream purification processes that enable the treatment of high cell density suspensions, preferably at lower cost, high reliability and increased simplicity as compared to methods described by others. This applies, in particular, to the field of recombinant protein and antibody production.

BRIEF SUMMARY

It has been found herein that crude cell culture harvests containing cells at high cell density, as well as secreted proteins, can be processed onto a TFF device without preliminary dilution. Although the crude cell culture harvests are very concentrated and contain high loads of cell debris, they were successfully clarified with no pressure build-up that led to blocking of the filter.

In addition, the process according to the disclosure is faster and cheaper than processes used hitherto. Expensive chromatography resins and long-lasting settling steps are no longer needed, and the process is easy to scale up.

This disclosure, therefore, relates to methods for the clarification of a crude cell culture harvest comprising cells, as well as a secreted desired protein, wherein the cells are at a cell density at harvest of at least $15 \times 10^6$ cells/ml and wherein at least 20% of the cells are viable, the method comprising the steps of:
 a. culturing cells in a bioreactor to a cell density of at least $15 \times 10^6$ cells/ml in order to obtain a crude cell culture harvest comprising desired secreted proteins;
 b. subsequently substantially processing the complete crude cell culture harvest obtained in step a) by tangential flow filtration (TFF), where the processed volume of the crude cell culture harvest is less than two times the volume of the bioreactor in which the crude cell culture harvest has been produced, and wherein the desired protein is separated from the crude cell broth; and
 c. recovering the desired protein in the filtrate.

In a preferred embodiment, the cell broth in step b) is subjected to TFF without preliminary dilution of the cell broth obtained in step a).

In some preferred embodiments, the cells are at a cell density at harvest of at least $50 \times 10^6$ cell/ml. In other preferred embodiments, the cells are at a cell density at harvest ranging between at least $50 \times 10^6$ cell/ml and $200 \times 10^6$ cell/ml.

In other preferred embodiments, the desired protein is a monoclonal antibody. In another preferred embodiment, the desired protein recovered in step b) is further purified.

In other preferred embodiments, the TFF is performed with a hollow fiber filter. The hollow fiber filter preferably comprises a pore size ranging between 750 KDa and 0.65 μm.

In other preferred embodiments, the hollow fiber filter in the TFF device comprises a lumen diameter ranging between 0.25 mm and 1 mm.

BRIEF DESCRIPTION OF THE DRAWING

FIG. 1. Experimental set-up.

DETAILED DESCRIPTION

This disclosure relates to methods for the clarification of a cell broth containing cells, as well as a secreted protein comprising high cell density. In the context of this disclosure, "crude cell culture harvest," "harvest," or "cell broth" means a cell culture inoculated with intact cells, and which may further contain culture medium as defined below, as well as secreted protein. Preferably, the cells are protein-secreting cells.

"Clarification" means the separation of solid material, such as the cells and cell debris, from the cell broth fluid. According to the disclosure, the secreted protein is present extracellularly and will thus be present in the cell broth fluid. In this disclosure, "clarification" means the separation of the secreted protein from the cell-containing crude cell culture harvest.

In the process of this disclosure, particularly when the cell density is extremely high, the starting material from the bioreactor is optionally diluted to a preferred cell density. However, the processed volume of the crude cell culture harvest according to the disclosure does not exceed twice the volume of the bioreactor in which the crude cell culture harvest has been produced. For the purpose of this disclosure, the so-diluted material is still covered by the terms "crude cell culture harvest" or "cell broth." Preferably, the crude cell culture harvest or cell broth is subjected to TFF without preliminary dilution of the crude cell culture harvest.

Moreover, according to this disclosure, it is substantially the complete crude cell culture harvest or cell broth obtained in step a) that is subsequently processed by TFF. "Substantially the complete crude cell culture harvest" means at least 70% of the entire crude cell culture harvest, preferably it means at least 80% of the entire crude cell culture harvest, more preferably at least 90% of the entire crude cell culture harvest and even more preferably at least 95% of the entire crude cell culture harvest.

With "secreted protein" used herein is meant protein that upon the production thereof, the cells are predominantly released (actively or passively) into the culture medium. With "desired" is meant herein that the protein is intentionally being produced making use of the cells.

"About" as used in the present application means ±10%, unless stated otherwise.

The crude cell culture harvest or cell broth that is clarified according to the method of the disclosure may be obtained by any cell culturing method suitable for attaining a cell density of the mammalian cells of at least $15 \times 10^6$ cells/ml. Suitable methods in this respect are described in, e.g., WO 2005/095578, WO 2004/099396 and WO 2008/006494. The contents thereof are incorporated herein by reference. According to the disclosure, the high cell density suspensions are obtained by culturing mammalian cells to high cell densities. Such culturing can be performed in (not limited) batch, fed-batch or perfusion mode.

In a preferred embodiment of this disclosure, the cell density in the crude cell culture harvest is at least about $15 \times 10^6$ cells/mL, e.g., at least about $20 \times 10^6$ cells/mL, e.g., at least about $25 \times 10^6$ cells/mL, e.g., at least about $30 \times 10^6$ cells/mL, e.g., at least about $40 \times 10^6$ cells/mL, e.g., at least about $50 \times 10^6$ cells/mL.

In another preferred embodiment of this disclosure, the cell density in the crude cell culture harvest is, e.g., up to about $150 \times 10^6$ cells/mL, e.g., up to about $200 \times 10^6$ cells/mL, e.g., up to about $250 \times 10^6$ cells/mL, e.g., up to about $300 \times 10^6$ cells/mL.

According to this disclosure, the clarified cell broth comprises cell densities ranging between $10 \times 10^6$ and $300 \times 10^6$ cells/mL, e.g., between about $15 \times 10^6$ and $250 \times 10^6$ cells/mL, e.g., between about $30 \times 10^6$ and $200 \times 10^6$ cells/mL, e.g., between about $50 \times 10^6$ and $150 \times 10^6$ cells/mL, e.g., between about $70 \times 10^6$ and $130 \times 10^6$ cells/mL, e.g., between about $90 \times 10^6$ and $110 \times 10^6$ cells/mL.

The cell density can be measured using a cell counter such as the Vi-CELL™ that uses the trypan blue exclusion method. Other suitable methods include cytometry, packed cell volume determination, or Coulter counters that use the Electrical Sensing Zone Method.

Moreover, in this disclosure, the viability of the cell culture prior to clarification remains higher than 20%. This means that at least 20% of the total amount of cells in the culture is viable at the start of the clarification process. In certain embodiments, the viability of the cell culture at the start of the clarification process is at least 40%, in further embodiments at least 60%, in further embodiments at least 80%, in further embodiments at least 90%. Viability can be measured using routine methods available to the skilled person, e.g., trypan blue exclusion, Casy cell count, and the like.

With "culture medium" is meant herein the extracellular environment of the cells that contains the nutrients and other constituents supporting the growth and production of cells, but may also contain waste products and/or host cell proteins (HCP) and/or material from lysed cells. The composition of the culture medium may vary in time during the course of the culturing of cells and, at the stage of clarification, may be depleted of one or more of the original constituents.

Once the proteins have been secreted in the cell culture, the proteins can be, according to this disclosure, purified from the high cell density suspension or crude cell culture harvest. The first step of such a purification of desired proteins is clarification of the crude cell culture harvest.

Clarification

The crude cell culture harvest obtained from the previous culturing step is subsequently clarified to remove precipitated impurities and cell debris. According to this disclosure, the clarification is performed with a TFF device. The TFF device preferably comprises a hollow fiber (see FIG. 1). Alternatively, the TFF device comprises a cassette filter. During clarification, the secreted protein is separated from the crude cell culture harvest with the tangential flow filtration device. The secreted protein is typically filtered tangentially through the filtration device and is recovered in the filtrate. Tangential flow filtration is a robust method of clarification of this disclosure.

In general, all types of hollow fiber filters can be used for the present application. In a preferred embodiment, the hollow fibers are the commonly used Discover, Explorer, Investigator and BioProducer filters from WaterSep. Other filters that are as well appropriate for the present method are the MidiKros, MINIKROS®, KROSFLO®, and CellFlo filters from Spectrum Labs. GE Healthcare also makes a very wide range of hollow fiber filters in PS (polysulfone). Preferred materials for the hollow fiber filters are polyethersulfone (PES), polysulfone (PS), modified polyethersulfone (m-PES), mixed cellulose ester (ME) or ceramic filters.

According to the disclosure, the filters can have different pore sizes. According to this disclosure, the hollow fibers comprise a pore size ranging between 250 kDa and 5 µm, e.g., between about 400 kDa and 4 µm, e.g., between about 500 kDa and 2.5 µm, e.g., between about 600 kDa and 1 µm. In a preferred embodiment, the pore size is ranging between 750 kDa and 0.65 µm.

In another preferred embodiment, the hollow fiber filter comprises a lumen diameter ranging between 0.1 and 6.0 mm, e.g., between 0.2 and 5 mm, e.g., between 0.2 and 3 mm, e.g., between 0.2 and 2 mm. In a preferred embodiment, the lumen diameter is ranging between 0.25 and 1 mm. In an even more preferred embodiment, the lumen diameter is about 0.5 mm.

The clarification method of this disclosure removes at least 70%, more likely at least 80%, or even preferably at least 90% of the whole cells and cell debris from the cell broth away from the suspension containing the desired proteins.

Following clarification of the crude cell culture harvest by tangential flow filtration, the desired proteins are recovered. With "recovery" is meant herein obtaining the desired product essentially free from cells and cell debris. According to this disclosure, the desired proteins are recovered in the filtrate of the TFF device. Cell debris and other impurities remain in the retentate.

Methods of Further Purification

In order to further purify the suspension comprising the desired proteins obtained from the steps described above, the skilled person is aware of, and can choose between, several purification steps. They comprise, e.g., filtration (such as depth filtration, microfiltration, ultrafiltration, diafiltration), chromatography (such as size exclusion chromatography, affinity chromatography, anion exchange chromatography, cation exchange chromatography, hydrophobic interaction chromatography, immobilized metal affinity chromatography), aqueous two-phase extraction, precipitation or centrifugation. Shulka et al., 2007 and Kelly et al., 2009 provide an overview of further purification steps that are commonly used in the art, in particular, for antibody purification.

In the case of immunoglobulins as the desired proteins, affinity chromatography, in particular, protein A chromatography, and cation exchange chromatography are especially suitable separation methods.

In certain embodiments according to the disclosure, the clarified suspension containing the desired proteins can be treated by ultrafiltration. Ultrafiltration is used to concentrate the suspension containing the desired proteins. The suspension can be concentrated 5 to 20 times.

In another embodiment of this disclosure, a buffer exchange is performed via diafiltration. Diafiltration, or buffer exchange, using ultrafilters is a way for removal and exchange of salts, sugars, and the like. The person skilled in the art knows under which conditions the buffer exchange should take place and which buffers are appropriate for this step.

In another embodiment of this disclosure, a following step can be an anion exchange chromatography step. During this step, proteins are bound to a positively charged material, e.g., a membrane, cartridge or column. Subsequent elution allows for separating the proteins from impurities and remaining host cell DNA. In yet another embodiment, the anion exchange chromatography step can be used as a flow-through system.

In certain embodiments, it is preferred to use at least one anion exchange chromatography step. After the anion exchange chromatography step, the proteins may be sufficiently pure. In certain embodiments, however, a size exclusion chromatography step is further performed to increase the robustness of the process. This step may be prior to or after the anion exchange chromatography step.

In any particular embodiment of this disclosure, the anion exchange product can be diafiltered into formulation buffer and sterile filtered. Alternatively, an additional chromatography step (e.g., cation exchange) may be added either before or after the diafiltration with the potential to improve the robustness of impurity and/or virus/prion clearance.

A sterile filtration step may be included in the process, which is helpful in eliminating bioburden. The product can be filtered through a 0.22 micron modified polyvinylidene fluoride (PVDF) membrane (e.g., MILLIPORE® and MILLIPAK®).

Scale of Cell Culture Systems and Downstream Processing Systems

The processes of this disclosure are scalable. The cell cultures used in this disclosure range from small-scale cultures (e.g., 1-10 liter runs) to medium-scale cultures (e.g., 10-1000 L runs) up to large commercial-scale preparations, such as 1000 to 10,000 L production runs. The tangential flow filtration step scales with culture volume, while the optional and subsequent steps, such as anion exchange chromatography, scale with the input of desired proteins.

Therefore, the size of the latter steps will be based on a bioreactor productivity estimate.

The purification of proteins from high-density crude cell culture harvest, which may contain high concentrations of proteins, is made possible with this disclosure. The possibility to process these cell suspensions, which contain high amounts of cell debris and host cell DNA, allow for the purification of high quantities of proteins, such as antibodies per volume of suspension. It is the merit of this disclosure to provide for a method for processing cell culture batches with high cell densities, containing high concentrations of desired proteins and therewith allowing for very high yields per processed volume. The present method, although it is applicable to large-scale cell cultures, will allow for cells to be cultured at smaller scale, yet to higher cell densities, and still reach high product yields, which can be efficiently further processed. This method offers the possibility to process highly concentrated batches of desired proteins, which will have a great impact on the entire biopharmaceutical purification industry.

Cells

Cells according to this disclosure can be any type of cells, preferably mammalian cells such as CHO (Chinese Hamster Ovary) cells, hybridomas, BHK (Baby Hamster Kidney) cells, myeloma cells, human cells, for example HEK-293 cells, human lymphoblastoid cells, PER.C6® cells, mouse cells, for example, NS0 cells, MDCK cells, Vero cells, amniocytes, duck cell lines, etc. In a preferred embodiment, the cells in the process of this disclosure are protein-secreting cells.

In another preferred embodiment, the cells in the process of this disclosure are PER.C6® cells or derivatives thereof (see U.S. Pat. Nos. 5,994,128 and 7,291,484, the entire content of each of which is incorporated by reference herein). PER.C6® cells are exemplified by cells as deposited under ECACC No. 96022940.

Secreted Proteins

Secreted proteins, which may be produced by the cells according to this disclosure (for example, by expressing a recombinant gene coding therefor), are, for example, recombinant proteins, in particular, receptors, enzymes, fusion proteins, blood proteins such as proteins from the blood coagulation cascade, multifunctional proteins such as, for instance, erythropoietin, virus or bacterial proteins, for instance, for use in vaccines; immunoglobulins such as, for example, IgG or IgM, and the like. A secreted protein according to this disclosure is more preferably an immunoglobulin or a part thereof and is produced by the cells. In a preferred embodiment, the secreted desired protein is a monoclonal antibody. Preferably, the proteins produced by the cells can be used as an active ingredient in a pharmaceutical preparation.

The disclosure is further explained in the following examples. The examples do not limit the disclosure in any way. They merely serve to clarify the disclosure.

EXAMPLES

Example 1

PER.C6® cells that express CR6261 antibody were cultured to a cell density of approximately $75 \times 10^6$ total cells/ml in a bioreactor at 37° C. in serum-free culture medium according to the method disclosed in WO 2008/006494. The cell viability at harvest was about 68%.

2L of crude cell culture harvest were filtered by tangential flow filtration through the hollow fiber at a shear rate of 4000 $s^{-1}$ until the inlet pressure began to rise sharply (corresponding to approximately $300 \times 10^6$ cells/ml in the retentate). The filter that was used in the TFF device was a 0.5 µm pore size hollow fiber filter from Spectrum Laboratories with 0.5 mm lumen diameter and 1050 cm² surface area (cat #M1-M05E-360-F1N).

In a following step, diafiltration was started. The retentate was washed with 3 diafiltration volumes of 1×PBS and then concentrated further until filtration was no longer possible due to the high inlet pressure.

The final cell concentration in the retentate was approximately $570 \times 10^6$ total cells/ml. The final permeate volume was 3064 g, the dilution factor was 1.6, and a product recovery of 81% was achieved. This shows that, surprisingly, the method of this disclosure is appropriate for the direct clarification of a cell culture harvest comprising high densities of antibody-producing cells.

Example 2

PER.C6® cells that express CR57 antibody were cultured to a cell density of approximately $82 \times 10^6$ total cells/ml in a bioreactor at 37° C. in serum-free culture medium according to the method disclosed in WO 2008/006494. The cell viability at harvest was about 58%.

One liter of crude cell culture harvest was filtered by tangential flow filtration through the hollow fiber at a shear rate of 4000 $s^{-1}$ until the inlet pressure began to rise sharply (corresponding to approximately $270 \times 10^6$ cells/ml in the retentate). The filter that was used in the TFF device was a 0.5 µm pore size hollow fiber filter from Spectrum Laboratories with 0.5 mm lumen diameter and 1050 cm² surface area (cat #M1-M05E-360-F1N).

In a following step, diafiltration was started. The retentate was washed with 3 diafiltration volumes of 1×PBS and then concentrated further until filtration was no longer possible due to the high inlet pressure.

The final cell concentration in the retentate was approximately $540 \times 10^6$ total cells/ml. The final permeate volume was 1755 g, so the dilution factor was 1.7, and a product recovery of 87% was achieved. This confirms that the method of this disclosure is appropriate for the direct clarification of a cell culture harvest comprising high densities of antibody-producing cells.

Example 3

PER.C6® cells that express CR8020 antibody were cultured to a cell density of approximately $194 \times 10^6$ total cells/ml in a bioreactor at 37° C. in serum-free culture medium according to the method disclosed in WO 2008/006494. The cell viability at harvest was about 85%.

One liter of crude cell culture harvest was filtered by tangential flow filtration through the hollow fiber at a shear rate of 4000 $s^{-1}$ until the inlet pressure began to rise sharply (corresponding to approximately $300 \times 10^6$ cells/ml in the retentate). The filter that was used in the TFF device was a 0.5 µm pore size hollow fiber filter from Spectrum Laboratories with 0.5 mm lumen diameter and 1050 cm² surface area (cat #M1-M05E-360-F1N).

In a following step, diafiltration was started. The retentate was washed with 3 diafiltration volumes of 1×PBS and then concentrated further until filtration was no longer possible due to the high inlet pressure.

The final cell concentration in the retentate was approximately $610 \times 10^6$ total cells/ml. The final permeate volume was 1780 g, so the dilution factor was 1.8, and a product recovery of 97% was achieved. This shows that surprisingly, even at high cell densities around 200×10⁶ total cells/ml, the method of this disclosure is appropriate for the direct clarification of the cell culture harvest comprising antibody-producing cells.

REFERENCES

Kamen and Henry, 2004. Development and optimization of an adenovirus production process. *J. Gene Med.* 2004; 6:S184-S192.

Kelley et al. *Process Scale Purification of Antibodies*, edited by Uwe Gottschalk, Copyright © 2009 John Wiley & Sons, Inc. Chapter 1: Downstream processing of monoclonal antibodies: current practices and future opportunities.

Morenweiser et al. Downstream processing of viral vectors and vaccines. *Gene Therapy* (2005) 12:S103-S110.

Schirmer B. et al. Primary Clarification of Very High-Density Cell Culture Harvests By Enhanced Cell Settling. *Bioprocess International*, January 2010, p. 32-39.

Shulka et al. Downstream processing of monoclonal antibodies—Application of platform approaches. *Journal of Chromatography B* (2007) 848:28-39.

van Reis R., L. C. Leonard, C. C. Hsu, and S. E. Builder. Industrial Scale Harvest of Proteins from Mammalian Cell Culture by Tangential Flow Filtration. *Biotechnology and Bioengineering*, Vol. 38, p. 413-422 (1991).

The invention claimed is:

1. A method for clarifying a crude cell culture harvest comprising cells as well as a secreted desired protein, wherein the cells are at a cell density at harvest of at least 15×10⁶ cells/ml and wherein at least 20% of said cells are viable, said method comprising the steps of:
   a. culturing cells in a bioreactor to a cell density of at least 15×10⁶ cells/ml in order to obtain a crude cell culture harvest comprising desired secreted proteins;
   b. subsequently processing at least 70% of the crude cell culture harvest obtained in step a) by tangential flow filtration (TFF) to form a crude cell broth, wherein the processed volume of said crude cell culture harvest is less than two times the volume of the bioreactor in which the crude cell culture harvest has been produced, and wherein the desired protein is separated from the crude cell broth; and
   c. recovering the desired protein in the filtrate.

2. The method according to claim 1, wherein the cells are at a cell density at harvest of at least 50×10⁶ cell/ml.

3. A The method according to claim 2, wherein the cells are at a cell density at harvest ranging between at least 50×10⁶ cell/ml and 200×10⁶ cell/ml.

4. The method according to claim 1, wherein the desired protein is a monoclonal antibody.

5. The method according to claim 1, wherein the desired protein recovered in step b) is further purified.

6. The method according to claim 1, wherein said TFF is performed with a hollow fiber filter.

7. The method according to claim 2, wherein the desired protein is a monoclonal antibody.

8. The method according to claim 3, wherein the desired protein is a monoclonal antibody.

9. The method according to claim 2, further comprising: further purifying the desired protein recovered in step c).

10. The method according to claim 3, further comprising: further purifying the desired protein recovered in step c).

11. The method according to claim 2, wherein the TFF is performed with a hollow fiber filter.

12. The method according to claim 3, wherein the TFF is performed with a hollow fiber filter.

13. The method according to claim 4, wherein the TFF is performed with a hollow fiber filter.

14. The method according to claim 7, wherein the TFF is performed with a hollow fiber filter.

15. The method according to claim 8, wherein the TFF is performed with a hollow fiber filter.

16. A method of recovering secreted monoclonal antibody from a crude cell culture harvest comprising cells and secreted monoclonal antibody, wherein the cells are at a cell density at harvest of at least 15×10⁶ cells/ml and wherein at least 20% of the cells are viable, the method comprising:
   culturing cells in a bioreactor to a cell density of at least 50×10⁶ cells/ml to form a crude cell culture harvest;
   processing at least 70% of the crude cell culture harvest by tangential flow filtration with a hollow fiber filter to form a crude cell broth, wherein the crude cell culture harvest's processed volume is less than two times the bioreactor's volume; and
   separating the secreted monoclonal antibody from the crude cell broth so as to recover the secreted monoclonal antibody.

17. The method according to claim 16, wherein the cells are at a cell density at harvest ranging between at least 50×10⁶ cell/ml and 200×10⁶ cell/ml.

* * * * *